US005861503A

United States Patent [19]
Barrio et al.

[11] Patent Number: 5,861,503
[45] Date of Patent: Jan. 19, 1999

[54] PROCESS FOR PRODUCING 8-FLUOROPURINES

[75] Inventors: Jorge R. Barrio, Agoura Hills; Nagichettiar Satyamurthy; Mohammad Namavari, both of Los Angeles; Michael E. Phelps, Encino, all of Calif.

[73] Assignee: The Regents of the University of California, Oakland, Calif.

[21] Appl. No.: 846,424

[22] Filed: Apr. 30, 1997

[51] Int. Cl.[6] .......................... C07H 19/16; C07D 473/00
[52] U.S. Cl. ...................... 536/27.11; 536/27.6; 536/27.8; 536/27.81; 544/264
[58] Field of Search ............................... 536/27.11, 27.6, 536/27.8, 27.81; 544/264

[56] References Cited

PUBLICATIONS

"Substitution and Additons in the Heterocyclic Rings of Nucleic Acid Bases and Their Derivative—§, Sub–section 1 (Halogenation)," in Ch. 5 of *Organic Chemistry of Nucleic Acids*, Part B, Kochetkov et al. (Russian eds.), Haigh et al. (English translator & eds.), Plenum Press, New York, NY, 1972, only pp. 269–275 supplied.

Goodman, "Chemical Synthese and Transformations of Nucleosides,", Ch. 2 in *Basic Principles in Nucleic Acid Chemistry*, vol. 1, Ts'o (ed.), Academic Press, New York, NY, 1974, only pp. 146–152 and 202 supplied.

Robins et al., "A Direct Synthesis of 5–Fluorocytosine and Its Nucleosides Using Trifluoromethyl Hypofluorite," *J. Chem. Soc.,* Part D(Chem. Comm.), (1), pp. 18–19, (Jan. 5, 1972).

Jorge R. Barrio, et al., Regioselective Fluorination of Substituted Guanines with Dilute $F_2$: A Facile Entry to 8–Fluoroguanine Derivates, *J. Org. Chem.*, 1996, 61, 6084–6085., Issue No. 18, Sep. 6, 1996.

Jorge R. Barrio, et al., "Elemental Fluorine to 8–Fluoropurines in One Step" *J. American Chem. Soc.*, 1996, 118, 10408–10411., Issue No. 43, Oct. 30 1996.

William Braker, et al., "Matheson Gas Data Book," Matheson Gas Products, East Rutherford, N.J. 1971,. pp. 261–265 only.

Sono, M., et al., "Functionalization Including Fluorination of Nitrogen–Containing Compounds Using Electrochemical Oxidation," *Chem. Pharm. Bull.*, vol. 44, No. 6, pp. 1141–1145 (Jun. 1996).

Jorge R. Barrio, et al., A Direct Method for the Preparation of 2–Hydroxyethoxymethly Derivatives of Guanine, Adenine, and Cytosine, *J. Med. Chem*, 1980, 23, 572–574, issue No. 5.

Ratsep, P., et al., "Introduction of Fluorine Into the C8 Position Of Purine Nucleosides," *Nucleosides & Nucleotides*, 1990, 9(2), pp. 197–204.

Pross, A., "A General Approach to Organic Reactivity: The Configuration Mixing Model," *Advances in Physical Organic Chemistry*, 1985, vol. 21, pp. 99–198.

Lacan, G., et al., "Fluorination of (E)–β–(Fluoromethylene)–m–Tyrosine: Regioselective Synthesis of 4–Fluoro–(E)–β–(Fluoromethylene)–m–Tyrosine," *J. Org. Chem.*, 1995, vol. 60, No. 1, pp. 227–234.

Barrio, Jorge R., et al., "A Direct Method for the Preparation of 2–Hydroxyethoxymethyl Derivatives of Guanine, Adenine, and Cytosine", *J. Med. Chem.*, 1980, vol. 23, No. 5, pp. 572–574.

Satyamurthy, N., et al., "Making $^{18}$F radiotracers for medical research," *Chemtech*, Mar. 1994, pp. 25–32.

Coenen, H.H., et al., "Regiospecific Aromatic Fluorodemetallation of Group IVb Metalloarenes Using Elemental Flourine or Acetyle Hypofluorite," *Journal of Fluorine Chemistry*, 1987, vol. 36, p. 63.

Walsh, C., "Fluorinated Substrate Analogs: Routes of Metabolism and Selective Toxicity," *In Advances in Enzymology*: Meister, A. Ed: John Wiley and Sons: New York, 1983: vol. 55 pp. 197–289.

Welch, J. T., "Advances in the Prepration of Biologically Active Organofluorine Compounds," *Tetrahedron*, 1987, vol. 43, No. 14, pp. 3123–3197.

Welch, J. T., Ed., American Chem. Soc.: Washington, DC "Selective Fluorination in Organic and Bioorganic Chemistry," *American Chemical Society*, Apr. 22, 1990.

Barnett, W.C., *CRC Critical Reviews in Biochemistry*, vol. 15, Issue 3, pp. 210–213.

Marquez, Victor E., et al., "Acid–Stable 2'–Fluoro Purine Dideoxynucleosides as Active Agents against HIV," *J. Med. Chem.*, 1990, vol. 33, No. 3, pp. 978–985.

Robins, M. J., et al., "Nucleic acid related compounds. 34. Non–aqueous diazotization with tert–butyl nitrite. Introduction of fluorine, chlorine, and bromine at C–2 of purine nucleosides," *Can. J. Chem.*, 1981, vol. 59, pp. 2608–2611.

Montgomery, J. A., et al., "Synthesis and Biological Evaluation of 2–Fluoro–8–azaadenosine and Related Compounds[1]", *J. Med. Chem.*, 1983, vol. 26, No. 10, pp. 1483–1489.

Secrist III, J.A., et al., "2–Fluoroformycin and 2–Aminoformycin. Synthesis and Biological Activity," *J. Med. Chem.*, 1985, vol. 28, No. 11, pp. 1740–1742.

Secrist III, J. A., et al., "Synthesis and Biochemical Properties of 8–Amino–6–fluoro–9–β–D–ribofuranosyl–9H–purine,"*J. Med. Chem.*, 1986, vol. 29, No. 10, pp. 2029.–2074.

Secrist III, J.A., "Synthesis and Biological Evaluations of Certain 2–Halo–2'–Substituted Derivatives of 9–β–D–Arabinofuranosyladenine," *J. Med. Chem.*, 1988, vol. 31, No. 2, pp. 405–410.

(List continued on next page.)

*Primary Examiner*—Douglas W. Robinson
*Assistant Examiner*—L. Eric Crane
*Attorney, Agent, or Firm*—Christie, Parker & Hale, LLP

[57] ABSTRACT

An efficient, regiocontrolled approach to the synthesis of 8-fluoropurines by direct fluorination of purines with dilute elemental fluorine, or acetyl hypofluorite, is provided. In a preferred embodiment, a purine compound is dissolved in a polar solvent and reacted with a dilute mixture of $F_2$ in He or other inert gas.

13 Claims, No Drawings

OTHER PUBLICATIONS

Robins, M. J., et al., "Nucleic Acid Related Compounds. III. A Facile Synthesis of 5–Fluorouracil Bases and Nucleosides by Direct Fluorination," *Journal of the American Chemical Society*, vol. 93, 1971, pp. 5277–5278 (Oct. 6, 1971).

Robins, M. J., et al., "Nucleic Aacid Related Compounds. 21. Direct Fluorination of Uracil and Cytosine Bases and Nucleosides Using Trifluoromethyl Hypoflourite. Mechanism, Stereochemistry, and Synthetic Applications," *Journal of the American Chemical Society*, 1976, vol. 98, p. 7381.(Nov. 10, 1976).

Gerstenberger, M.R.C., et al., "Methods of Fluorination in Organic Chemistry," *Angew. Chem. Int. Ed. Engl.*, 1981, vol. 20, p. 647.

Beaman, A. G., et al., "The Direct Conversion of Chloropurines to Fluoropurines," *J. Org. Chem.*, 1963, vol. 28, pp. 2310–2313.

Naik, S. R., et al., "A Novel Route to 3(5)–Fluoro–1,2, 4–triazoles and 8–Fluoropurines by Displacement of the Nitro Group," *J. Org. Chem.*, 1973, vol. 38, No. 25, pp. 4353–4354.

Ikehara, M., et al., "Studies of Nucleosides and Nucleotides. XLIX. Synthesis of 8–Fluoroadenosine," *Chem. Pharm. Bull.*, 1971, vol. 19, pp. 104–109. Issue No. 1.

Kobayashi, Y., et al., "Synthesis of 2',3', 5'–Tris–O–acetyle–8–fluoroadenosine," *J.C.S. Chem. Comm.*, 1976, pp. 430–431.

Sono, M., et al., "Functionalisation Including Fluorination of Caffeine, Guanosine Tetraacetate, and Uridine Triacetate using Electrochemical Oxidation," *Tetrahedron Letters*, 1994, vol. 35, No. 49, pp. 9237–9238.

Rozen, S., "The formation of the C–F bond: the last twelve years," *Supplement D2: The chemistry of halides, pseudo–halides and azides*, Patai, S. et al. Eds: John Wiley and Sons: Chichester, U.K. 1995; Chapter 12, pp. 629–708.

Rozen, S., et al., "Remote and Selective Electrophilic Fluorinations at the Carbon–Hydrogen Single Bond," *J. Am. Chem. Soc.*, 1980, vol. 102, No. 22, pp. 6860–6861.

Shiue, C., et al., "A New Improved Synthesis of 2–Deoxy–2–[$^{18}$F]Fluoro–D–Glucose from $^{18}$F–Labeled Acetyl Hypofluorite," *The Journal of Nuclear Medicine*, 1982, vol. 23, No. 10, pp. 899–903.

Kosower, E. M., et al., "Bimanes. 21. syn–(Methyl,fluoro-)bimane, Formation via Acetyl Hypofluorite," *J. Org. Chem.*, 1985, vol. 50, No. 21, pp. 4152–4154.

Luxen, A., et al., "Electrophilic And Nucleophilic Approaches to the Synthesis of 3–Fluorodiazepam," *Journal of Fluorine Chemistry*, 1987, 36, pp. 83–92.

Bryce, M. R., et al., "Electrophilic fluorination of tin and mercury derivatives as a route to fluoroaromatics," *Bulletin De La Societe Chimique De France*, 1986. No. 6, pp. 930–932.

Fused Pyrimides, Brown, D.J. Ed., Part II, Purines; Meister, J.H. Ed.; Wiley–Interscience: New York, 1971, Chapter V, pp. 136.–201.

Stolarski, R., et al., "Comparison Of Theoretical and Experimental Approaches To Determination of Conformation of Nucleosides About The Glycosidic Bond," *Biochimica et Biophysica Acta*, 1980, 610, pp. 1–19.

Silverman, R.B. in Mechanism–Based Enzyme Inactivation: Chemistry and Enzymology; CRC Press, Inc.: Boca Raton, FL, 1988; vol. 1, pp. 59–93.

Mario Ikehara and Tohikazu Fukui, Studies of Nucleosides and Nucleotides. LVIII*.Deamination of Adenosine Analogs with Calf Intestine Adenosine Deaminase, Biochemical et Biophysica Acta, vol. 338, 1974; 512–519.

PROCESS FOR PRODUCING 8-FLUOROPURINES

ACKNOWLEDGMENT OF GOVERNMENT SUPPORT

This invention was made with government support under Grant No. DE-FC0387-ER60615, awarded by the Department of Energy. The government has certain rights in the invention.

FIELD OF INVENTION

The present invention relates to synthetic methods for making fluoropurines, particularly 8-fluoropurines, and their derivatives.

BACKGROUND OF INVENTION

During the last four decades, interest in fluorinated purine and pyrimidine derivatives has grown, driven by their potential use as anti-cancer and anti-viral agents and the unique properties displayed by fluorine-substituted bioactive molecules. In terms of size, replacement of hydrogen for fluorine would produce minimum stearic perturbations upon the binding of the analogue molecules to receptors or enzymes. Fluorine has a small van der Waals radius (1.35Å), which closely resembles that of hydrogen (1.2Å). However, the strong electron-withdrawing properties of fluorine may substantially, yet in a predictable manner, alter the chemical stability or enzymatic activity of substrate molecules. In addition, the carbon-fluorine bond is energetically more stable than the carbon-hydrogen bond.

Although the fluorine atom has been successfully introduced at the 2- and 6-positions of the purine ring system and the sugar moiety of related nucleosides, access to 8-fluoropurines and derivatives has remained limited. The absence of successful syntheses of 8-fluoropurines using elemental fluorine is quite conspicuous, as other halogens—chlorine, iodine, and particularly bromine—have been successfully used in their elemental form to produce regiospecific substitution of the C(8)-hydrogen of purines. Indeed, in many instances, the use of elemental halogen has been the most convenient procedure for regiospecific C(8)-halogen substitution.

Earlier approaches to 8-fluoropurines have been limited to a few reports, involving nucleophilic displacements, Schiemann reactions, halogen exchange reactions, and electrochemical oxidations. None of the synthetic methods involve the use of elemental fluorine or similar agents (e.g., acetyl hypofluorite) that have been successfully used in the synthesis of substituted and unsubstituted 5-fluorouracil and 5-fluorocytosine. Indeed, an attempted fluorination of an oxopurine with phosphoryl fluoride was unsuccessful.

Because of the burgeoning interest in fluorine-substituted bioactive molecules and the numerous failed attempts of others, a need exists for an effective, straightforward synthetic method for making 8-fluoropurines and related derivatives, such as 8-fluoroguanine and 8-fluoropurinylnucleosides.

SUMMARY OF THE INVENTION

The present invention provides an effective synthetic method for making 8-fluoropurines and related compounds, and essentially comprises the step of introducing elemental fluorine or acetyl hypofluorite into a solution containing a substituted or unsubstituted purine compound. Preferably, the reaction is carried out in a polar solvent, which lowers the activation energy of the transition state intermediate and provides a hydrogen acceptor to the counterion of the electrophile (e.g., fluoride ion with $F_2$, and acetate ion for AcOF). Despite the fact that monofluorinations of aromatic substrates with elemental fluorine (or AcOF) are unfavored and frequently require the directing effects of Group IVA metals (Si,Ge,Sn), the fluorination reaction of the present invention unexpectedly proceeds readily and in moderate yield, making it very attractive to produce otherwise inaccessible 8-fluoropurine derivatives.

Elemental fluorine or acetyl hypofluorite is conveniently introduced into the solution as a dilute stream in an inert gas. Isolated yields of 8-fluorinated purine compounds as high as 30% have been realized with the new method.

This reliable and direct synthetic approach now makes accessible a variety of 8-fluoro-substituted purines for determination of their biochemical and pharmacological properties. As an indication of the potential of these derivatives, the ability of an 8-fluoroacycloguanine derivative to act as a substrate for HSV tk has already provided a new approach to monitor gene expression in-vivo.

DETAILED DESCRIPTION OF THE INVENTION

Purine is a nitrogenous base having the following formula and numbering system:

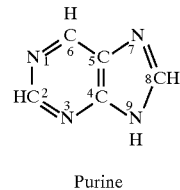

Purine

The present invention provides an effective, one-step synthesis of 8-fluoropurines using elemental fluorine. In a preferred embodiment, 8-fluoropurine compounds are prepared by bubbling a dilute stream of fluorine or acetyl hypofluorite gas into a solution containing a substituted or unsubstituted purine compound. The reaction proceeds regioselectively, with the C(8)-fluorinated derivative being the major product isolated, in moderate yields.

Although fluorine and acetyl hypofluorite are highly toxic and reactive gases, they can be handled safely by following known procedures developed specifically for such gases (see e.g., *Matheson Gas Data Book*, Braker, W., Mossman, A. L., Eds.; Matheson, East Rutherford, N.J., 1971; p.261) and the fluorination reaction can be run using ordinary glassware.

It is preferred to introduce fluorine (or its derivative, acetyl hypofluorite) into the reaction vessel as a dilute mixture with an inert gas. Nonlimiting examples of inert gases suitable for use in the present invention include noble gases like He, Ar, etc., as well as nitrogen ($N_2$,), with He and $N_2$ being preferred. The fluorination reaction proceeds readily even at fluorine concentrations as low as 1% by volume. The flow rate of the $F_2$/He mixture is controlled to assure a fine dispersion of the gas mixture in the solvents used. Good results are seen with flow rates of approximately 5–10 $\mu$mol of $F_2$/min). Progress of the reaction can be monitored by TLC, $^1$H NMR, and $^{19}$F NMR. Typically, disappearance of the C(8)-hydrogen singlet at 7.7 at 8.0 ppm in $^1$H NMR and the concomitant appearance of a singlet in the $^{19}$F NMR at, e.g., −102.3 to −108.2 ppm, enables the progress of the reaction to be followed and, incidentally, confirms a reaction at carbon-8 of the purine ring.

It is also preferred to run the reaction in a polar solvent. Although not bound by theory, a key element in the success of the fluorination reaction appears to reside in the modulation of the electrophilic character of fluorine reactivity. The use of polar solvents for the fluorination reactions lowers the activation energy of the transition state intermediate below that of homolytic cleavage of the F—F bond (39 kcal/mol). It also provides a hydrogen acceptor to the counterion of the electrophile (e.g. fluoride ion with $F_2$ and acetate ion for AcOF).

Although the use of polar solvents for fluorine substitution reactions has been reported for the synthesis of 5-fluorouracil and its nucleosides, and in the controlled fluorination of benzoate esters, similar aromatic substitutions with dilute elemental fluorine (<than 1% $F_2$ in $N_2$) in solvents favoring homolytic $F_2$ cleavage (e.g., $CFCl_3$) produced very low yields (<0.1%) of fluorinated products.

Non-limiting examples of polar solvents suitable for use in the present invention include water, dimethyl sulfoxide, acetonitrile, lower alkyl short chain alcohols (e.g., ethanol), lower alkyl carboxylic acids (e.g., acetic acid) and lower alkyl chlorinated hydrocarbons (e.g., chloroform). As used herein, the term "lower alkyl" means a straight or branched alkyl group having from 1 to 6 carbon atoms. The solubility of the purinyl reactant, or course, can dictate the choice of solvent; unprotected purines such as β-D-ribofuranosyl-guanine and (2-hydroxyethoxymethyl)guanine, for example, are not particularly soluble in chloroform, but can be fluorinated in ethanol (EtOH) with acceptable results. The addition of base, for example, a tetraalkylammonium hydroxide, such as tetraethylammonium hydroxide, improved their solubility in EtOH.

A large variety of 8-fluoropurines, including 8-fluoro derivatives of adenine, guanine, and their related nucleosides, can be prepared using the method provided by the present invention. Of particular interest are 8-fluoro-9-substituted purine nucleosides, and their precursors. Starting with a substituted or unsubstituted purine of formula 1, reaction with elemental fluorine (or acetyl hypofluorite) yields an 8-fluoro purine compound of formula 2:

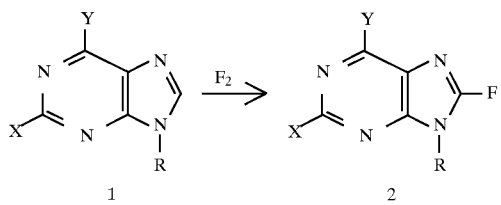

where, for example, X and Y independently are alkyl, aryl, arylalkyl, alkoxy, aryloxy, acetyl, amino (forming a primary, secondary or tertiary amine of formula 1 or formula 2), substituted amino, protected amino carbamoyl, alkoxyamino, aryloxyamino, alkylcarbonylamino, alkoxyacetylamino, aryloxyacetylamino, benzoylamino, tritylamino, halogen, hydroxy, or hydrogen, and R is alkyl, aryl, arylalkyl, hydrogen, ribofuranosyl, protected ribofuranosyl (e.g., tri-O- acetyl-ribofuranosyl), modified protected or unprotected ribofuranosyl (e.g., deoxyribofuranosyl, dideoxyribofuranosyl, also having protecting groups such as trityl, substituted trityl, aryloxyacetyl and alkyloxyacetyl), hydroxyalkoxy lower alkyl (e.g., (2-hydroxyethoxy) methyl), or protected hydroxyalkoxy lower alkyl (e.g., (2-acetoxyethoxy)methyl), where lower alkyl is as defined above; wherein each alkyl or aryl moiety independently can be unsubstituted or substituted with one or more of hydroxy, halogen, lower alkyl or lower alkoxy. It will be appreciated that, when X or Y is hydroxy, oxo-species (=O) are also generally present, as a result of tautomerism with the hydroxy(lactim). In aqueous solutions, the cyclic amide tautomer predominates.

The term "substituted amino" includes, without limitation, amino groups and protected amino groups including such groups as alkylamino, arylamino, alkoxyamino, carbamoyl, aryloxyamino, alkylcarbonylamino, alkoxyacetylamino, aryloxyacetylamino, benzoylamino, and tritylamino, where each alkyl or aryl moiety independently can be unsubstituted or substituted with one or more of hydroxy, halogen, lower alkyl or lower alkoxy.

The term "protected" in "protected ribufuranosyl" and "protected hydroxyalkoxy lower alkyl" refers to the substitution of a protective group, such as acetyl ($CH_3CO$—), for the proton(s) of one or more hydroxyl groups or amino groups in the chemical moiety of interest, for the purpose of preventing a reaction at the hydroxyl or amino functionality. The protective group(s) can be removed later in a "deprotection" step, by treatment with ammonia or inorganic bases such as NaOH, KOH, etc., in lower alkyl alcohols (e.g., ethanol, methanol, etc.), cyclic ethers, or acyclic ethers.

Table 1 provides a representative, nonlimiting list of 8-fluoropurines of formula 2, prepared according to the present invention. $^1$H and $^{19}$F chemical shift data are presented in Table 2.

TABLE 1

Examples of 8-Fluoropurine Compounds

| Compound[a] | R | X | Y | Isolated Yields (%) |
|---|---|---|---|---|
| 2a | β-D-ribofuranosyl | $NH_2$ | OH | 7 |
| 2b | 2',3',5'-tri-O-acetyl-β-D-ribofuranosyl | NHAc | OH | 30 |
| 2c[b] | (2-hydroxyethoxy)methyl | $NH_2$ | OH | 10 |
| 2d | (2-acetoxyethoxy)methyl | NHAc | OH | 28 |
| 2e | 2',3',5'-tri-O-acetyl-β-D-ribofuranosyl | H | OH | 27 |
| 2f | 2',3',5'-tri-O-acetyl-β-D-ribofuranosyl | H | $NH_2$ | 25 |

[a]The cyclic amide tautomers of the indicated hydroxy(lactim) heterocycles predominate in aqueous solution.
[b]Reaction also performed with acetyl hypofluorite in HOAc (see the Experimental Section).

TABLE 2

$^{19}$F and $^1$H NMR Chemical Shifts for Purine and Anomeric (or N-$CH_2$-O) Protons

| | $^{19}$F NMR[a] | $^1$H NMR | | | |
|---|---|---|---|---|---|
| Compound | C(8)-F | C(8)-H | C(2)-H | C(1')-H | Solvent |
| 1a | | 7.93 | | 5.68 | DMSO-$d_6$ |
| 2a | −102.3 | | | 5.61 | DMSO-$d_6$ |
| 1b | | 7.77 | | 6.10 | $CDCl_3$ |
| 2b | −107.5 | | | 6.08 | $CDCl_3$ |
| 1c | | 7.80[b] | | 5.33[c,d] | DMSO-$d_6$ |
| 2c | −108.2 | | | 5.32[c,d] | DMSO-$d_6$ |
| 1d | | 7.78 | | 5.47[c] | $CDCl_3$ |
| 2d | −107.8 | | | 5.39[c] | $CDCl_3$ |
| 1e | | 8.00 | 8.26 | 6.15 | $CDCl_3$ |
| 2e | −103.3 | | 8.20 | 6.05 | $CDCl_3$ |

TABLE 2-continued

19F and 1H NMR Chemical Shifts for Purine and Anomeric (or N-CH$_2$-O) Protons

| Compound | 19F NMR[a] C(8)-F | 1H NMR C(8)-H | C(2)-H | C(1')-H | Solvent |
|---|---|---|---|---|---|
| 1f | | 7.95 | 8.36 | 6.17 | CDCl$_3$ |
| 2f | −102.9 | | 8.34 | 6.05 | CDCl$_3$ |

[a]Typical chemical shifts for fluoropurines are as follows: C(2)-F, −50 ppm; C(6)-F, −60 to −79 ppm.
[b]C(8)-H chemical shift in CD$_3$OD: 7.76.
[c]Chemical shifts for the N-CH$_2$-O protons (singlet).
[d]C(1')-H chemical shifts in CD$_3$OD: 1c, 5.40; 2c, 5.32.

Although protected oxopurines (such as compounds (1b, d, e, above) and adenosine (1f) all react cleanly with F$_2$, providing a route to the corresponding 8-fluoro counterparts (i.e., 2b, d, e, f) in 25–30% isolated yields, unreacted starting material ($\geq$20%) was always present at the end of the reaction. Attempts to consume most of the starting material (s) lead to a decrease in the isolated 8-fluorinated product yields, presumably due to multiple fluorination and/or formation of oxidation products. For example, in the fluorination of 9-(2', 3', 5',-tri-O-acetyl-β-D-ribofuranosyl)-adenine, a biproduct with a molecular weight of 446 (FAB MS) and a 19F NMR chemical shift of −51.24 was also observed. The isolated product yields reported herein reflect these conditions.

For reactions with purines such as 1a, c in ethanol, larger amounts of starting material can be recovered from the reaction mixture. Longer reaction times, however, revealed the formation of side products in detriment to the yield of C(8)-fluorinated products. Although the reaction can be run in solvents such as water and acetic acid (HOAc), yields are generally much lower than that observed in ethanol.

In an alternate embodiment, acetyl hypofluoride (AcOF) is used in place of elemental fluorine for selective C(8)-hydrogen substitution of purine derivatives. The milder AcOF (generated in-situ according to the method of Shiue, C.-Y., et al., *J. Nucl. Med.* 1982, 23 899) also reacts with purine compounds, but with lower efficiency. In contrast, attempts to fluorinate substituted purines with XeF$_2$ and other fluorinating agents failed. Reactions of various purine compounds with XeF$_2$, N-fluoropyridinium triflate, N-fluor-3,5-dichloropyridinium triflate, N-fluor-2,4,6- trimethylpyridinium triflate, and N-fluor-N-(chloromethyl) triethylenediamine bis (tetrafluoroborate), a Select fluor reagent, were all unsuccessful.

EXAMPLES

The following nonlimiting examples are illustrative of the invention.

Experimental Methods

Melting points were determined on an electrothermal melting point apparatus and are uncorrected. 1H, 13C, and 19F NMR spectra were recorded with a 360 MHz instrument. 1H and 13C chemical shifts are expressed in parts per million downfield from tetramethylsilane (TMS). 19F chemical shifts are referenced to an external fluorotrichloromethane standard. The concentrations of all the samples for NMR analysis were maintained at 50 mM. Electron impact and direct chemical ionization (DCI) high-resolution mass spectral (HRMS) data were recorded on a VG Analytical Autospec mass spectrometer. Fast atom bombardment (FAB) high-resolution mass spectral data were obtained on a ZAB SE mass spectrometer. Preparative HPLC purification was carried out on a Beckman 110 system equipped with a UV detector. Ultraviolet spectra were recorded with a Beckman DU-640 spectrophotometer. TLC were run on silica gel plates (Whatman PE SIL G/UV) in CHCl$_3$:CH$_3$OH:H$_2$O. Solvent proportions were as follows: 1a, 2a, 1c, 2c (60:36:4); 1b, 2b, 1d, 2d (80:18:2); 1f, 2f (90:9:1); and 1e, 2e (100% EtOAc).

Fluorination reactions were run in ordinary glassware, following known precautions for handling fluorine and acetyl hypofluorite (see, *Matheson Gas Data Book*, supra).

Direct Fluorination of Unprotected Purine Nucleosides with F$_2$. Fluorine (1% in He, 0.6 mmol) was bubbled into a solution of the unprotected purine derivative (0.3 mmol) in absolute ethanol (6.0 mL) and tetraethylammonioum hydroxide (0.34 mL of 20% aqueous solution) at room temperature over a period of 1 h. The reaction mixture was neutralized with 1N HOAc (0.46 mL), concentrated, and chromatographed on a silica gel (CHCl$_3$:CH$_3$OH:H$_2$O= 90:9:1). Earlier fractions contained the required fluoro analogue, and from the later fractions, the unreacted starting material was recovered. Fractions containing product were pooled, and the solvents were evaporated to give the 8-fluoropurine nucleoside analogue, which was further purified by preparative HPLC (column: Alltech Econosil. C-18, 5µ, 50×1 cm; mobile phase: 5% CH$_3$OH in water, flow rate: 5 mL/min; UV: 254 nm).

8-Fluoro-9-[(2-hydroxyethoxy)methyl)]guanine (8-Fluoroacyclovir) (2c). 10% isolated yield (52% yield based on the starting material recovered); mp 212° C. (dec). 1H NMR (CD$_3$OD): δ 3.53–3.62 (m, 4H), 5.31 (s, 2H) ppm. UV (H$_2$O)λ$_{max}$(H$_2$O): 242 nm (ε 9530), 275 (7100). Electron impact HRMS calcd for C$_8$H$_{10}$N$_5$O$_3$F: 243.0768. Found: 243.0772.

8-Fluoroguanosine (2a). 7% yield (46% yield based on the starting material recovered); mp 238° C. (dec). 1H NMR (DMSO-d$_6$): δ 3.42–3.56 (m, 2H), 3.81–3.84, 4.02–4.06 (2m, 2H), 4.54–4.59 (m, 1H), 4.88 (t, J=5.8 Hz, 1H), 5.15 (d, J=5.0 Hz, 1H), 5.49 (d, J=5.7 Hz, 1H), 5.61 (d, J=6.6 Hz, 1H), 6.58 (br s, 2H), 10.83 (br s, 1H) ppm. UV (methanol) λ$_{max}$(H$_2$O): 243 nm (ε 9500), 275 (7100). FAB HRMS (M$^+$H)$^+$ calcd for C$_{10}$H$_{13}$N$_5$O$_5$F: 302.0901. Found: 302.0905.

Fluorination of Acyclovir (1c) with AcOF. To a solution of AcOF [prepared by bubbling of 0.12 mmol of 1% F$_2$ in He into a solution of aqueous ammonium hydroxide (0.03 mL) in glacial acetic acid (5 mL)] was added 25 mg of acyclovir (2c) (0.11 mmol) in 1 mL of acetic acid. The reaction mixture was stirred at room temperature for 15 min and evaporated to dryness. 8-fluoroacyclovir (1c) (5% isolated yield; 43% yield based on the starting material recovered) was purified by column chromatography followed by preparative HPLC (see above).

Direct Fluorination of Protected Purine Nucleosides with F$_2$. Fluorine (1% in He, 0.6 mmol) was bubbled into a solution of the protected purine derivative (1b,d,e,f) (0.4 mmol) in CHCl$_3$ (6.0 mL) at room temperature over a period of 1 h. The reaction mixture was concentrated and chromatographed (silica gel). The initial fraction afforded the fluoronucleoside, and from the later fractions, the unreacted starting material was recovered.

N$_2$-Acetyl-8-fluoro-9-[(2-acetoxyethoxy)methyl]guanine (2d). Acetonitrile was used as the solvent for the fluorination. Chromatography eluent: CHCl$_3$:CH$_3$OH:H$_2$O (95:4.5:0.5); 28% yield; mp 196°–198° C. 1H NMR (CD$_3$OD): δ 1.97 (s, 3H), 2.23 (s, 3H), 3.82 (t, J=4.5 Hz, 2H), 4.15 (t, J=4.5 Hz, 2H), 5.47 (s, 2H) ppm. 13C NMR (DMSO-d$_6$): δ 20.38, 23.70, 62.53, 67.08, 70.97, 113.50 (d, J=12.2 Hz), 147.29, 148.68, 149.31 (d, J=244.1 Hz), 153.92, 170.09, 173.53 ppm. DCI HRS $(M^+H)^+$ calcd for $C_{12}H_{15}N_5O_5F$: 328.1057. Found: 328.1056.

$N_2$, 2',3',5'-Tetraacetyl-8-fluoroguanosine (2b). Chromatography eluent: $CHCl_3:CH_3OH:H_2O=98:1.8:0.2$; 30% yield (yield based on the recovered starting material: 37%); mp 89°–92° C. $^1H$ NMR $(CDCl_3)$: δ 2.06 (s, 3H), 2.11 (s, 3H), 2.16 (s, 3H), 2.32 (s, 3H, 4.41(dd, J=11.0 and 7.1 Hz, 1H), 4.48 (q, J=5.4 Hz, 1H), 4.69 (dd, J=11.0 and 4.8 Hz, 1H), 5.85 (t, J=4.6 Hz, 1H), 6.06 (t, J=5.2 Hz, 1H), 6.08 (d, J=5.4 Hz, 1H) ppm. $^{13}C$ NMR $(CDCl_3)$: δ 20.40, 20.60, 20.89, 24.23, 63.09, 70.93, 72.33, 80.02, 85.52, 115.81 (d, J=14.2 Hz), 145.67, 147.68, 149.06 (d, J=250.0 Hz), 154.46, 169.48, 169.87, 171.74, 171.89 ppm. These data are in agreement with literature values.

2',3',5'-Tri-O-acetyl-8-fluoroadenosine (2f). Chromatography eluent: EtOAc:hexane (3:1); 25% yield; mp 98°–101° C. $^1H$ NMR $(CDCl_3)$: δ 2.08 (s, 6H), 2.15 (s, 3H), 4.29 (dd, J=12.1 and 5.0 Hz, 1H), 4.39 (q, J=4.5 Hz, 1H), 4.48 (dd, J=12.1 and 3.5 Hz, 1H), 5.73 (t, J=5.4 Hz, 1H), 5.79 (br s, 2H), 6.05 (d, J=5.6 Hz, 1H), 6.07 (t, J=5.3 Hz, 1H), 8.34 (s, 1H) ppm. $^{13}C$ NMR $(CDCl_3)$: δ 20.42, 20.56, 20.67, 62.95, 70.52, 71.96, 80.39, 85.04, 114.24 (d, J=12.2 Hz), 148.68 (d, J=4.0 Hz), 150.83 (d, J=254.5 Hz), 152.86 (d, J=3.4 Hz), 154.34, 169.47, 169.58, 170.55 ppm, FAB HRMS $(M+H)^+$ calcd for $C_{16}H_{19}N_5O_7F$: 412.1268. Found: 412.1264. These data are in agreement literature values.

2',3',5'-Tri-O-acetyl-8-fluoroinosine (2e). Chromatography eluent: EtOAc:hexane (9:1); 27% yield; mp 80°–83° C. $^1H$ NMR $(CDCl_3)$: δ 2.10 (s, 3H), 2.11 (s, 3H), 2.16 (s, 3H), 4.29 (dd, J=11.9 and 4.9 Hz, 1H), 4.39 (q, J=4.5 Hz, 1H), 4.47 (dd, J=11.9 and 3.5 Hz, 1H), 5.65 (t, J=5.5 Hz, 1H), 6.02–6.05 (m, 2H), 8.20 (s, 1H), 13.02 (br s, 1H) ppm. $^{13}C$ NMR $(CDCl_3)$: δ 20.31, 20.46, 20.61, 62.82, 70.30, 71.89, 80.34, 85.20, 119.55 (d, J=12.3 Hz), 145.28, 147.24 (d, J=3.7 Hz), 150.07 (d, J=252.9 Hz), 157.74, 169.32, 169.47, 170.39 ppm. FAB HRMS $(M+H)^+$ calcd for $C_{16}H_{18}N_4O_8F$: 413.1109. Found: 413.1104.

General Procedure for Deprotection of 2b, d. To the protected 8-fluoropurine derivative (2b,d) (0.1 mmol) was added a solution of methanolic ammonia (5 mL of 2M solution), and the reaction mixture was stirred at room temperature. The solution was evaporated to dryness, and the residue was purified by column chromatography as described above to provide the deblocked 8-fluoronucleosides (2a: reaction time 5 h, 50% yield; 2c: reaction time 2–4 h, 30% yield). Literature precedence indicates for a nucleophilic displacement of C(8)-F in methanolic ammonia. Under the experimental conditions for deprotection, 2b,d defluorinated with a $t_{1/2}$ of decomposition of about 5 h. Defluorination was easily demonstrated with [$^{18}$F] radiofluorinated 2b,d. Appearance of [$^{18}$F] fluoride ion, disappearance of starting materials (2b,d), and product formation (2a,c) was verified by radio thin layer chromatography (silica gel, $CHCl_3:CH_3OH:H_2O$, 60:36:4)). Optimum reaction times for product (2a,c) isolation varied from 2 to 5 h. Radiofluorinated 2b,c,d were synthesized by bubbling cyclotron-produced [$^{18}$F]$F_2$ (Bishop, A. J.; Satyamurthy, N.: Bida. G. T.; Hendry. G.; Phelps. M. E.; Barrio. J. R. *Nucl Med. Biol.* 1996, 23. 189) (1% in Ar) with 1b,c, d, respectively (specific activity: 2.5 Ci/mmol; $t_{1/2}$ of $^{18}$F is 109.7 min).

Effects of C(8) Fluorine Substitution on Bioactivity

The lack of easy access to 8-fluoropurines has limited the understanding of their biochemical and pharmacological properties. It could be conjectured, however, that the electronegative effects of the fluorine atom at C(8) in these analogues may be significant on the substrate activity of 8-fluoropurine ribosides with several enzymes (e.g., N-ribosylhydrolases and transferases) that cleave the C-N ribosidic bond by an $S_N1$-like mechanism.

To gain insight into the biological significance of 8-fluoro substitution, the specificity of 2c for Herpes Simplex Virus I thymidine kinase was demonstrated with the use of fluorine-18-labeled 2c to image with positron emission tomography the expression of HSV tk transplanted genes in living animals. See, Srinivasan, A., et al., *J. Nucl. Med.* 1996 37, 107P.

Given the anti-viral, anti-cancer, and other pharmaceutical applications of various fluoropurine derivatives recently made available, it appears likely that 8-fluoropurines, now made possible by the present invention, will show similar bioactivity and benefit. The above-described specificity of 2c for HSV tk is just one example. Preliminary indications suggest that 8-fluoro substitution in purine nucleosides (or their analogs) in general increases the stability of the $C_1$.—Ng bond. This observation will have significant impact in the in-vivo use of the anti-HIV therapeutic drug, ddI (available from Bristol-Myers Squibb), which is known to have poor in-vivo stability.

All cited references are incorporated herein as if set forth in their entirety.

What is claimed is:

1. A method of making an 8-fluoropurine compound, comprising:
   introducing elemental fluorine or acetyl hypofluorite into a solution containing a purine compound.

2. A method as recited in claim 1, wherein the purine compound is dissolved in a polar solvent.

3. A method as recited in claim 2, wherein the polar solvent is selected from the group consisting of water, dimethyl sulfoxide, acetonitrile, lower alkyl alcohols, lower alkyl carboxylic acids, and lower alkyl chlorinated hydrocarbons.

4. A method as recited in claim 2, wherein the polar solvent is selected from the group consisting of ethanol, chloroform, and acetic acid.

5. A method as recited in claim 3, wherein the polar solvent is ethanol.

6. A method as recited in claim 1, wherein the solution also contains a base.

7. A method as recited in claim 6, wherein the base is a tetraalkylammonium hydroxide.

8. A method as recited in claim 1, wherein the purine compound has the formula

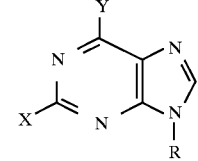

where X and Y independently are alkyl, aryl, arylalkyl, alkoxy, aryloxy, acetyl, amino, substituted amino, protected amino, carbarnoyl, alkoxyamino, aryloxyamino, alkylcarbonylamino, alkoxyacetylamino, aryloxyacetylamino, benzoylamino, tritylamino, halogen, hydroxy, or hydrogen;

R is alkyl, aryl, arylalkyl, hydrogen, ribofuranosyl, protected ribofuranosyl, deoxyribofuranosyl, dideoxyribofuranosyl, hydroxyalkoxy lower alkyl, or protected hydroxyalkoxy lower alkyl; and each alkyl or aryl moiety independently is unsubstituted or substituted with one or more of hydroxy, halogen, lower alkyl or lower alkoxy.

9. A method as recited in claim 1, wherein elemental fluorine or acetyl hypofluorite is introduced as a dilute mixture with an inert gas.

10. A method as recited in claim 9, wherein the inert gas is helium, argon or nitrogen.

11. A method of making an 8-fluoropurine compound of the formula

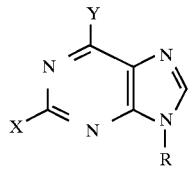

where X and Y independently are alkyl, aryl, arylalkyl, alkoxy, aryloxy, acetyl, amino, substituted amino, protected amino, carbamoyl, alkoxyamino, aryloxyamino, alkylcarbonylamino, alkoxyacetylamino, aryloxyacetylaiio, benzoylamino, tritylamino, halogen, hydroxy, or hydrogen;

R is alkyl, aryl, arylalkyl, hydrogen, ribofuranosyl, protected ribofuranosyl, deoxyribofuranosyl, dideoxyribofuranosyl, hydroxyalkoxy lower alkyl, or protected hydroxyalkoxy lower alkyl, and each alkyl or aryl moiety independently is unsubstituted or substituted with one or more of hydroxy, halogen, lower alkyl or lower alkoxy, comprising;

reacting, in a polar solvent, a purine compound of the formula

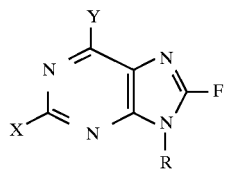

where X, Y and R are as recited above,
with elemental fluorine or acetyl hypofluorite mixed with an inert gas.

12. A method as recited in claim 10, farther comprising passing the reaction mixture through a chromatographic column and evaporating the solvent.

13. A method for making an 8-fluoropurine compound, comprising:
replacing hydrogen with fluorine at the C(8) position of a purine compound by reacting the purine compound with elemental fluorine ($F_2$) or acetyl hypofluorite.

* * * * *

UNITED STATES PATENT AND TRADEMARK OFFICE
CERTIFICATE OF CORRECTION

PATENT NO. : 5,861,503
DATED : January 9, 1999
INVENTOR(S) : Jorge R. Barrio et al.

It is certified that error appears in the above-identified patent and that said Letters Patent is hereby corrected as shown below:

Title page,
Item [56], References Cited, OTHER PUBLICATIONS,
The first publication listed should read -- Substitution and Additions in the Heterocyclic Rings of Nucleic Acid Bases and Their Derivative—§II,.... --
Insert the following publications:

-- ZUPAN, M., "Functionalization of organic molecules by xenon fluorides," Supplement D2: *The chemistry of halides, pseudo-halides and azides,* Patai, S., et al. Eds: John Wiley and Sons: Chichester, U.K. 1995, Chapter 15, pp. 821-860.

UMEMOTO, T., ET AL., "Power and Structure-Variable Fluorinating Agents. The N-Fluoropyridinium Salt System," *J. Am. Chem. Soc.,* 1990, vol. 112, No. 23, pp. 8563-8575.

LAL, G.S., "Site-Selective Fluorination of Organic Compounds Using 1-Alkyl-4-fluoro-1,4-diazabicyclo[2.2.2]octane Salts (Selectfluor Reagents)," *J. Org. Chem.,* 1993, vol. 58, No. 10, pp. 2791-2796.

GAL, C., ET AL., "Activation of Tertiary Paraffins by Elemental Fluorine," *Tetrahedron Letters,* 1984, vol. 25, No. 4, pp. 449-452.

ROSEN, S., ET AL., "Activating Unreactive Sites of Organic Molecules Using Elemental Fluorine," *J. Org. Chem.,* 1987, vol. 52, No. 13, pp. 2769-2779.

ROZEN, S., "Elemental Fluorine as a 'Legitimate' Reagent for selective fluorination of Organic Compounds," *Acc. Chem. Res.,* 1988, vol. 21, pp. 307-312.

CECH, D., ET AL., "Preparation of Some 2'-Deoxy-5-Fluorouridine Derivatives By A Direct Fluorination*," *Collection Czechoslov. Chem. Commun.,* 1976, vol. 41, pp. 3335-3342.

PURRINGTON, S., ET AL., "The Application of Elemental Fluorine in Organic Synthesis," *Chem. Rev.,* 1986, vol. 86, No. 6, pp. 997-1018.

UNITED STATES PATENT AND TRADEMARK OFFICE
CERTIFICATE OF CORRECTION

PATENT NO.   : 5,861,503
DATED        : January 9, 1999
INVENTOR(S)  : Jorge R. Barrio et al.

It is certified that error appears in the above-identified patent and that said Letters Patent is hereby corrected as shown below:

GRAKAUSKAS, V., "Direct Liquid-Phase Fluorination of Aromatic Compounds," *J. Amer. Chem. Soc.*, vol. 35, No. 3, pp. 723-728 (March 1970).

CACACE, F., ET AL., "Substrate Selectivity and Orientation in Aromatic Substitution by Molecular Fluorine," *Journal of the American Chemical Society*, 1980, vol. 102. pp. 3511-3515.

NAMAVARI, M., ET AL., "Regioselective Radiofluorodestanylation with [$^{18}$F]F$_2$ and [$^{18}$F]CH$_3$COOF: a High Yield Synthesis of 6-[$^{18}$F]Fluoro-L-dopa," *Appl. Radiat. Isot.*, 1992, vol. 43, No. 8, pp. 989-996.

NAMAVARI, M., ET AL., "Synthesis of 6-[$^{18}$F] and 4-[$^{18}$F]Fluoro-L-m-tyrosines via Regioselective Radiofluorodestannylation," *Appl. Radiat. Isot.*, 1993, vol. 44, No. 3, pp. 527-536.

MODESTO OROZCO, ET AL., "Quantum Chemical Study of the Electronic and Conformational Characteristics of Adenosine and 8-Substituted Derivatives: Functional Implications in the Mechanism of Reaction of Adenosine Deaminase," *Journal of Pharmaceutical Sciences*, vol. 79, No. 2, pp. 133-137 (2/1990).

MORRIS J. ROBINS, ET AL., "Nucleic Acid Related Compounds. 47. Synthesis and Biological Activities of Pyrimidine and Purine "Acryuclic" Nucleoside Analogues," *J. Med. Chem.*, 1984, vol. 27, 1486-1492, Issue No. 11.

VAN DER PUY, M., ET AL., "Controlled, Regiospecific Oxidation of Pyridine Carboxylic Acids and Esters With Elemental Fluorine" *Tetrahedron Letters*, 1988, vol. 29, N. 35, pp. 4389-4392. --

Column 2,
Line 61, after "F$_2$min" delete ")".

Column 3,
Line 15, replace "(<than 1%" with -- (< 1% --.

UNITED STATES PATENT AND TRADEMARK OFFICE
CERTIFICATE OF CORRECTION

PATENT NO.   : 5,861,503
DATED        : January 9, 1999
INVENTOR(S)  : Jorge R. Barrio et al.

It is certified that error appears in the above-identified patent and that said Letters Patent is hereby corrected as shown below:

Column 6,
Line 13, replace "tetraethylammonioum" with -- tetraethylammonium --.

Column 8,
Line 19, replace "Ng" with -- $N_9$ --.
Line 57, replace "carbarnoyl" with -- carbamoyl --.

Column 9,
Line 19, replace "aryloxyacetylaiio" with -- aryloxyacetylamino --.

Column 10,
Line 16, replace "farther" with -- further --.

Signed and Sealed this

Twenty-eighth Day of January, 2003

JAMES E. ROGAN
*Director of the United States Patent and Trademark Office*